United States Patent [19]

Kraus et al.

[11] Patent Number: 5,459,273
[45] Date of Patent: Oct. 17, 1995

[54] PROCESS FOR THE PREPARATION OF 2-HALOGENO-5-CYANO PYRIDINES

[75] Inventors: Helmut Kraus, Odenthal; Hans-Joachim Traenckner, Leverkusen, both of Germany

[73] Assignee: Bayer Aktiengesellschaft, Leverkusen, Germany

[21] Appl. No.: 207,734

[22] Filed: Mar. 8, 1994

[30] Foreign Application Priority Data

Mar. 15, 1993 [DE] Germany ............. 43 08 152.5

[51] Int. Cl.⁶ ............. C07D 413/04; C07D 213/09; C07D 213/84
[52] U.S. Cl. ............. 546/250; 544/124; 546/193; 546/281; 546/286
[58] Field of Search ............. 546/286, 250, 546/281, 193; 544/124

[56] References Cited

U.S. PATENT DOCUMENTS

| | | | |
|---|---|---|---|
| 4,404,388 | 9/1983 | Fäh et al. | 546/345 |
| 4,678,795 | 7/1987 | Shiokawa et al. | 514/341 |
| 4,738,924 | 4/1988 | Kulla et al. | 435/121 |
| 4,774,247 | 9/1988 | Shiokawa et al. | 514/256 |
| 4,812,571 | 3/1989 | Shiokawa et al. | 546/296 |

FOREIGN PATENT DOCUMENTS

| | | |
|---|---|---|
| 0376279 | 7/1990 | European Pat. Off. . |
| 0425030 | 5/1991 | European Pat. Off. . |
| 3726993 | 2/1989 | Germany . |

OTHER PUBLICATIONS

Chemical Abstract; 27–Heterocycles, p. 639, vol. 103, 1985; CA#71193W: "2–Chloronicotinic acid", F. Nagy et al.
Chemical Abstract, p. 742, vol. 111, 1989; CA#57553x: "Preparation of α–halopyridine derivatives by photochemical halogenation", K. Suzuki et al.
Y. Hiroshi et al, "Site selectivity in the reaction of 3–substituted pyridine 1–oxides with phosphoryl chloride", Chem. Abstr. 192171r, V. 110, No. 21, (1989) p. 685.

*Primary Examiner*—Alan L. Rotman
*Attorney, Agent, or Firm*—Sprung Horn Kramer & Woods

[57] ABSTRACT

The title compounds of the formula

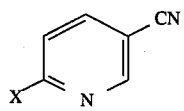 (I)

can be prepared by reacting methylene-glutaconic acid dinitriles of the formula $R^1$—CH=C(CN)—CH'CH—CN     (II)

with hydrogen halide of the formula

HX     (III)

In these formulae,

X denotes fluorine, chlorine, bromine or iodine and
$R^1$ denotes —$OR^2$ or —$N(R^2, R^3)$,
  in which $R^2$ and $R^3$, independently of one another, represent straight-chain or branched $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl, $C_6$–$C_{12}$-aryl, $C_7$–$C_{10}$-aralkyl or a 5- to 8-membered saturated or unsaturated heterocyclic ring containing 1 or 2 heteroatoms from the group comprising N, O and S, where $R^2$ and $R^3$, with the N atom on which they are substituents, may also form a 5- to 8-membered ring which may contain a further heteroatom from the group comprising N, O and S.

8 Claims, No Drawings

PROCESS FOR THE PREPARATION OF 2-HALOGENO-5-CYANO PYRIDINES

The invention relates to a process for the preparation of 2-halogeno-5-cyano-pyridines by reacting methyleneglutaconic acid dinitriles with hydrogen halide.

Compounds of the abovementioned type, for example 2-chloro-5-cyano-pyridine, are important intermediates for 2-chloro-5-aminomethylpyridine (German Offenlegungsschrift 37 26 993) and 2-chloro-5-chloromethyl-pyridine, which in turn represent key compounds in the production of insecticides of the nitromethylene class (EP 163 855, EP 376 279, EP 425 030).

The chlorination of nicotinic acid N-oxide derivatives takes place preferentially in the 2 position (HU 33 464; cited in C.A. 103 (1985), 71 193 w), whereas exposing nicotinoyl chloride to light while passing in a 15-fold excess of gaseous chlorine gibes 6-chloro-nicotinic acid in addition to the 2-chloro derivative (JP 01/42 467 (1989); cited in C.A. 111 (1989), 57 553 x). Furthermore, 6-chloro-nicotinic acid can also be obtained by bacterial hydroxylation followed by chlorination (EP 152 949, EP 72 777). However, because of the inadequate space-time yields and the troublesome separation of isomers, both processes are poorly suited to an industrial implementation.

It was therefore surprising that the cyclization of methylene-glutaconic acid dinitriles with hydrogen halide gives 2-halogeno-5-cyano-pyridines in high yields and free from isomers.

A process has been found for the preparation of 2-halogeno-5-cyano-pyridines of the formula

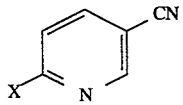 (I)

in which
X represents fluorine, chlorine, bromine or iodine,
which is characterized in that methylene-glutaconic acid dinitriles of the formula

in which
$R^1$ represents $-OR^2$ or $-N(R^2,R^3)$,
in which $R^2$ and $R^3$, independently of one another, represent straight-chain or branched $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl, $C_6$–$C_{12}$-aryl, $C_7$–$C_{10}$-aralkyl or a 5- to 8-membered saturated or unsaturated heterocyclic ring containing 1 or 2 heteroatoms from the group comprising N, O and S, where $R^2$ and $R^3$, with the N atom on which they are substituents, may also form a 5- to 8-membered ring which may contain a further heteroatom from the group comprising N, O and S, are reacted with hydrogen halide of the formula

in which
X has the above meaning.

Straight-chain or branched $C_1$–$C_8$-alkyl is, for example, methyl, ethyl, propyl, isopropyl, butyl, isobutyl, tertbutyl, the isomeric pentyls, hexyls or octyls, preferably the $C_1$–$C_4$-alkyl radicals mentioned.

Straight-chain or branched $C_3$–$C_8$-alkenyl is, for example, allyl, the isomeric butenyls, pentenyls, hexenyls or octenyls, preferably the $C_3$–$C_4$-alkenyl radicals mentioned.

Straight-chain or branched $C_2$–$C_8$-alkoxyalkyl is, for example, methoxymethyl, ethoxymethyl and other radicals from the group $C_3$–$C_9$-alkyl, in which a $CH_2$ group is replaced by an O atom.

Straight-chain or branched $C_4$–$C_8$-alkoxyalkenyl is, for example, methoxyallyl, 2-methoxy-propenyl and others from the group $C_4$–$C_9$-alkenyl, in which a $CH_2$ group is replaced by an O atom.

$C_3$–$C_8$-cycloalkyl is, for example, cyclopropyl, methylcyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl or cyclooctyl, preferably cyclopropyl, cyclopentyl and cyclohexyl, and their methyl or dimethyl derivatives.

$C_6$–$C_{12}$-aryl is, for example, phenyl, naphthyl or biphenylyl, preferably phenyl.

$C_7$–$C_{10}$-aralkyl is, for example, benzyl, 1-phenylethyl, 2-phenylethyl and other radicals of this type which are known to those skilled in the art, preferably benzyl.

The 5- to 8-membered saturated or unsaturated heterocyclic ring containing 1 or 2 heteroatoms from the group comprising N, O and S may be: pyrrole, furan, thiophene, pyrrolidine, pyrazole, imidazole, thiazole, oxazole, pyridine, pyrimidine, piperazine which may be substituted on the N atom by $C_1$–$C_4$-alkyl or by hydroxy-$C_1$–$C_4$-alkyl, morpholine, pyran, azepine, azocine, isoxazole, isothiazole, pyridazine and pyrazine. Those skilled in the art are aware that unsaturated heterocyclic rings may have a more or less pronounced aromatic character. Preferred possibilities for such saturated or unsaturated heterocyclic rings are morpholine, pyrrolidine and piperidine which may be substituted by $C_1$–$C_4$-alkyl or by hydroxy-$C_1$–$C_4$-alkyl.

It is also possible for $R^2$ and $R^3$, together with the N atom on which they are substituents, to form a 5- to 8-membered saturated or unsaturated ring which may contain a further heteroatom from the group comprising N, O and S. Examples of such rings are the abovementioned heterocycles.

Preferably, the methylene-glutaconic acid dinitriles employed in the method according to the invention are those in which the place of $R^2$, $R^3$ is taken by the substituents $R^{12}$, $R^{13}$ which, independently of one another, denote straight-chain or branched $C_1$–$C_8$-alkyl, cyclopropyl, cyclopentyl, cyclohexyl, phenyl or benzyl, where $R^{12}$ and $R^{13}$ may also, together with the N atom on which they are substituents, form a 5- to 8-membered ring which may contain a further heteroatom from the group comprising N, O and S.

Particularly preferably, the enamines employed in the process according to the invention are those in which the place of $R^{12}$, $R^{13}$ is taken by the substituents $R^{22}$, $R^{23}$ which, independently of one another, denote $C_1$–$C_4$-alkyl, where also $R^{22}$ and $R^{23}$, together with the N atom on which they are substituents, denote morpholine, pyrrolidine or piperidine which may be substituted by $C_1$–$C_4$-alkyl or by hydroxy-$C_1$–$C_4$-alkyl.

Preferably, the place of $R^1$ is taken by the substituent $R^{11}$ having the meaning $-N(R^2,R^3)$, where $R^2$ and $R^3$, independently of one another, have the meaning given earlier.

Also preferably, the place of X is taken by the substituent $X^1$ having the meaning chlorine or bromine, and it is particularly preferable for the place of $X^1$ to be taken by the substituent chlorine.

The reaction according to the invention can be represented, by way of example, as follows:

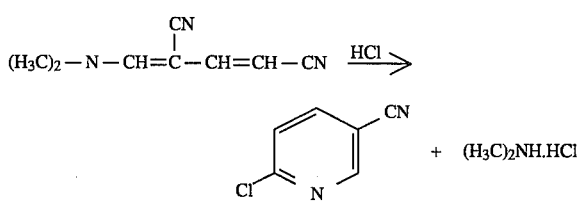

The reaction is carried out at a temperature of from −10° to 80° C., preferably at from 20°–60° C. The duration of the reaction depends on the temperature and diluent and is from 30 min to 5 h. The hydrogen halide is employed in a 1 to 40-fold excess, but preferably 1 to 10-fold. The cyclization takes place in solvents from the group comprising carboxylic acids, carboxamides, alcohols, ketones, ethers, (halogenated) aliphatic compounds and aromatic compounds. Individual examples of such solvents, which may also be employed as a mixture, are: acetic acid, propionic acid, dimethylacetamide, dimethylformamide (DMF), N-methylpyrrolidone, ethanol, butanol, acetone, methyl isobutyl ketone, methyl tert-butyl ether, anisole, tetrahydrofuran, chloroform, chloroethane, dichloroethane, petroleum ether, toluene and chlorobenzene. When it is intended to carry out the reaction in the absence of water, it is possible to add to the reaction medium some acid anhydride, such as acetic anhydride.

In a preferred embodiment, a mixture is used of a protonatable carbonyl compound such as, for example, acetic acid or dimethylformamide and an inert solvent, for example toluene or chloroform.

The $C_6$ unit, methylene-glutaconic acid dinitrile, is metered, in bulk or dissolved in one of the solvents mentioned, into a solution of HF, HCl, HBr or HI. The converse variant is also possible.

Following a short after-reaction time, excess cyclization reagent and the solvent are removed by distillation.

Where the starting material chosen was an enamine, a calculated quantity of water is added to the residue so as to obtain a relatively concentrated aqueous solution of the amine hydrohalide. The product is insoluble therein and can be obtained by filtration.

On the cyclization, the enamine may also be employed in the form of the crude product solution, which, because of its preparation (German Offenlegungsschrift 43 01 238), may contain an equivalent of the corresponding amine salt, for example a solution of dimethylaminomethyleneglutacononitrile and dimethylammonium acetate in glacial acetic acid.

If the parameters for the reaction are exceeded, it is possible for some of the cyanopyridine formed to react further to give the carboxamide. The latter can be converted back to the nitrile again with, for example, $POCl_3$.

EXAMPLES

Example 1

150 ml of 1,2-dichloroethane were saturated with HCl gas. While the introduction of HCl was continued, a hot saturated solution at 60° C. of 30 g of β-dimethylaminomethyleneglutacononitrile (DIMER) in 1,2-$Cl_2$-ethane was added dropwise at 50° C. over a period of 1 h. After a further hour of passing in HCl (slight breakthrough), the mixture was concentrated and 20 ml of water were added to the residue. After neutralization with saturated $NaHCO_3$ solution, the product was filtered off with suction and washed. 20.7 g of 83.2% pure 2-chloro-5-cyanopyridine were obtained, corresponding to 60.9% of the theoretical yield. After recrystallization from ethanol, crystals with a melting point of 116° C. were obtained. $^1$H-NMR (DMSO): 7.82 (d); 8.40 (dd); 8.95 (dd).

Example 2

Analogously to Example 1, 250 ml of solvent were initially introduced and DIMER was added in portions as a solid. Chlorocyanopyridine was obtained in 52.9% of the theoretical yield.

Example 3

200 ml of DMF were saturated with HCl gas at 50° C. While continuing to pass in HCl, 30 g of DIMER were metered in with a metering screw over a period of 1 h. Following an after-reaction time of 15 min, the mixture was concentrated and worked up analogously to Example 1. 25.3 g of 87.1% pure product were obtained, corresponding to 78.0% of the theoretical yield.

Example 4

13.2 g of β-dimethylamino-acrylonitrile were added dropwise at 30° C. to a solution of 22 g of DMF/HCl adduct in 100 ml of DMF. Following an after-reaction time of 2 h, this solution was added dropwise, while passing in HCl, to a solution, saturated at 50° C., of HCl gas in DMF. The temperature was maintained at 50° C. by cooling. After conventional work up (40 ml of water), 2-chloro-5-cyanopyridine was obtained in 77.7% of the theoretical yield, based on the $C_3$ unit employed.

Example 5

Analogously to Example 3, a solution, saturated at 50° C., of DIMER in DMF was added dropwise. The yield was 87.5% of the theoretical yield.

Example 6

Analogously to Example 1, 180 ml of 1,2-dichloroethane and 20 ml of DMF were initially introduced. 2-Chloro-5-cyanopyridine was obtained in 89.4% of the theoretical yield.

Example 7

The reaction was carried out analogously to Example 6 at 70° C. A mixture was obtained of 2-chloro-5-cyanopyridine, the carboxamide and the N-formyl-carboxamide. This mixture was reacted with $POCl_3$ in analogy to Soc. 1948, 1959. After recrystallization from petroleum ether, pure 2-chloro-5-cyanopyridine was obtained in 72.1% of the theoretical yield, as overall yield.

Example 8

A mixture of 195 ml of glacial acetic acid and 5 ml of acetic anhydride was saturated with HCl gas at 20° C. Over a period of 1 h, 30 g of DIMER were added using a metering screw. HCl gas was then passed in for a further 30 min and the batch was concentrated. After being stirred together with 70 ml of water and neutralized with $NaHCO_3$ solution, the product was filtered off and washed with water. The solid consisted of 41.3% of the theoretical yield of 2-chloro-5-cyanopyridine and 23.8% of the carboxamide.

Example 9

Analogously to Example 8, DIMER was metered into 200 ml of a 30% strength solution of HBr in glacial acetic acid. By GC/MS coupling, 2-bromo-5-cyanopyridine was identified as the main product.

Example 10

A solution of 30 g of ethoxymethylene-glutacononitrile in 300 ml of glacial acetic acid was cooled to 0° C. and saturated with HCl gas. The mixture was allowed to rise to room temperature and left to stand overnight. It was concentrated and the residue was stirred together with 70 ml of water and neutralized with NaHCO₃ solution. After being filtered off and recrystallized from ethanol, 2-chloro-5-cyanopyridine was obtained in 73.5% of the theoretical yield.

Example 11

Analogously to Example 5, pyrrolidinomethylene-glutacononitrile was cyclized with HCl gas. 2-Chloro-5-cyanopyridine was obtained in 83.3% of the theoretical yield.

We claim:

1. Process for the preparation of 2-halogeno-5-cyanopyridines of the formula

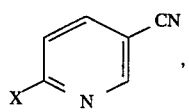

in which

X represents fluorine, chlorine, bromine or iodine, wherein methylene-glutaconic acid dinitriles of the formula

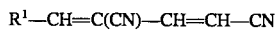

in which $R^1$ represents —$OR^2$ or —$N(R^2,R^3)$, in which $R^2$ and $R^3$, independently of one another, represent straight-chain or branched $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl, $C_6$–$C_{12}$-aryl, $C_7$–$C_{10}$-aralkyl or a 5- to 8-membered saturated or unsaturated heterocyclic ring containing 1 or 2 heteroatoms from the group comprising N, O and S, where $R^2$ and $R^3$, with the N atom on which they are substituents, may also form a 5- to 8-membered ring which may contain a further heteroatom from the group comprising N, O and S, are reacted with hydrogen halide of the formula

HX in which

X has the above meaning.

2. Process according to claim 1, wherein the place of $R^2$ and $R^3$ is taken by the substituents $R^{12}$ and $R^{13}$ which, independently of one another, denote straight-chain or branched $C_1$–$C_8$-alkyl, cyclopropyl, cyclopentyl, cyclohexyl, phenyl or benzyl, where $R^{12}$ and $R^{13}$ may also, together with the N atom on which they are substituents, form a 5- to 8-membered ring which may contain a further heteroatom from the group comprising N, O and S.

3. Process according to claim 2, wherein the place of $R^{12}$ and $R^{13}$ is taken by the substituents $R^{22}$, $R^{23}$ which, independently of one another, denote $C_1$–$C_4$-alkyl, where also $R^{22}$ and $R^{23}$, together with the N atom on which they are substituents, denote morpholine, pyrrolidine or piperidine which may be substituted by $C_1$–$C_4$-alkyl or by hydroxy-$C_1$–$C_4$-alkyl.

4. Process according to claim 1, wherein the place of $R^1$ is taken by the substituent $R^{11}$ having the meaning —$N(R^2, R^3)$, where $R^2$ and $R^3$, independently of one another, have the meaning given earlier.

5. Process according to claim 1, wherein the reaction is carried out at a temperature of from −10° C. to +80° C., preferably at from 20° to 60° C.

6. Process according to claim 1, wherein the reaction is carried out with from 1 to 40 mol, preferably from 1 to 10 mol, of hydrogen halide per mole of methylene-glutaconic acid dinitrile.

7. Process according to claim 1, wherein the reaction is carried out in a solvent from the group comprising carboxylic acids, carboxamides, alcohols, Ketches, ethers, aliphatic and aromatic (halogeno)hydrocarbons or a mixture thereof.

8. Process according to claim 1, wherein the place of X is taken by the substituent $X^1$ having the meaning chlorine or bromine and in that, preferably, the place of $X^1$ is taken by the substituent chlorine.

\* \* \* \* \*